(12) United States Patent
Guth et al.

(10) Patent No.: US 8,597,694 B2
(45) Date of Patent: Dec. 3, 2013

(54) STABILIZED OLEOSOME PREPARATIONS AND METHODS OF MAKING THEM

(75) Inventors: Jacob Guth, Upper Black Eddy, PA (US); Joseph Boothe, Calgary (CA); Mitch Beazer, Calgary (CA); Kent Shafer, Calgary (CA)

(73) Assignee: Sembiosys Genetics, Inc., Alberta (CA)

( * ) Notice: Subject to any disclaimer, the term of this patent is extended or adjusted under 35 U.S.C. 154(b) by 0 days.

(21) Appl. No.: 12/935,888

(22) PCT Filed: Apr. 10, 2009

(86) PCT No.: PCT/US2009/002243
§ 371 (c)(1),
(2), (4) Date: Dec. 2, 2010

(87) PCT Pub. No.: WO2009/126302
PCT Pub. Date: Oct. 15, 2009

(65) Prior Publication Data
US 2011/0081435 A1    Apr. 7, 2011

Related U.S. Application Data

(60) Provisional application No. 61/044,141, filed on Apr. 11, 2008.

(51) Int. Cl.
*A01N 65/00*    (2009.01)

(52) U.S. Cl.
USPC ............................................................ 424/725

(58) Field of Classification Search
None
See application file for complete search history.

(56) References Cited

U.S. PATENT DOCUMENTS

| | | | |
|---|---|---|---|
| 6,344,206 B1 * | 2/2002 | Nguyen et al. | 424/401 |
| 6,599,513 B2 | 7/2003 | Deckers et al. | |
| 2002/0071852 A1 | 6/2002 | Deckers et al. | |
| 2008/0241082 A1 * | 10/2008 | Guth et al. | 424/59 |

FOREIGN PATENT DOCUMENTS

WO    WO 98-53698 A1    12/1998

OTHER PUBLICATIONS

International Search Report PCT/US2009/002243 filed Dec. 9, 2009.
A.H.C. Huang et al., "Seed oil bodies in maize and other species", Botanical Bulletin of Academia Sinica, 1993, vol. 34, pp. 287-297.

* cited by examiner

*Primary Examiner* — Michael Meller
(74) *Attorney, Agent, or Firm* — Foley & Lardner LLP

(57) ABSTRACT

The physical stability of oleosomes is preserved in a composition by introducing a multihydric alcohol and an acid that can reduce the pH of the composition of less than 6. The resultant composition can be useful in the manufacture of cosmetic, food, and pharmaceutical products, among others.

3 Claims, No Drawings

STABILIZED OLEOSOME PREPARATIONS AND METHODS OF MAKING THEM

CROSS-REFERENCE TO RELATED APPLICATIONS

This application is the U.S. National Phase of PCT/US2009/002243 filed Apr. 10, 2009, which claims priority from U.S. Provisional Application No. 61/044,141 filed Apr. 11, 2008. The subject matter of each of the above-referenced applications is incorporated in entirety by reference.

FIELD OF THE INVENTION

The present invention relates to novel, oleosome-comprising compositions and to methodology for making them. These compositions are useful in relation to products for skin-topical application to the human body.

BACKGROUND OF THE INVENTION

Plant seed oils, such as palm oil, sunflower oil and rapeseed (Canola) oil, are a major agricultural commodity worldwide with a large variety of industrial and nutritional uses. More than 15 billion pounds of plant seed oil are produced annually in the United States alone. Wallis J., et al., "Seed oils and their metabolic engineering," in: SEED TECHNOLOGY AND ITS BIOLOGICAL BASIS, M. Black & J. D. Bewley (eds.), Sheffield Biological Sciences (2000). Ninety eight percent of the plant seed oil production in the United States is used is for nutritional purposes, such as in the manufacture of cooking oil and margarine. The balance of plant oils are used as raw materials in the manufacture of industrial products such as soaps, plasticizers, polymers, surfactants and lubricants.

Plant oils are triacylglycerols, i.e., a glycerol moiety in which each of the hydroxyl groups is esterified to a fatty acid. The glycerol backbone of the triacyl glycerol is invariable in structure, but the fatty acids attached to the glycerol vary considerably depending on the plant oil.

The structure of the fatty acid determines the physical and chemical properties of the plant oil. For example, the number of double bonds in a fatty acid, a variable frequently referred to as the "degree of unsaturation," affects the melting point of oils, while the chain length of a fatty acid affects its viscosity, lubricity and solubility.

Triacylglycerol molecules are insoluble in aqueous environments and tend to coalesce into oil droplets. In order to store these water insoluble triacylglycerols, plants have developed unique seed oil storage compartments of approximately 1-10 μm in diameter within the plant seed cells, variously known as "oil bodies," "oleosomes," "lipid bodies," and "spherosomes" (collectively, "oleosomes"). See Huang, *Ann. Rev. Plant Mol. Biol.* 43: 177-200 (1992). In addition to plant oil, these oleosomes comprise two chemical constituents: phospholipids and a class of proteins, known to the art as oil body proteins. From a structural standpoint, oleosomes are a triacylglycerol core encapsulated by a half unit membrane of phospholipids, in which the oil body proteins are embedded. Oil body proteins are believed to play a role in preventing the oleosomes from coalescing into much larger oil droplets.

For extraction of extract plant oils, the seeds are crushed or pressed and then refined using processes typically involving the use of organic solvents to separate the plant oil from other seed constituents, such as seed proteins and carbohydrates. Non-organic solvent-based plant oil extraction methodologies also have been developed, as described, for example, by Embong and Jelen, *Can. Inst. Food Sci. Techn. J.* 10: 239-43 (1977).

Since the primary objective of these extraction processes is to obtain pure plant oil, however, they typically disrupt oleosome structural. Thus, conventional compositions prepared from plant oils generally do not comprise intact oleosomes.

For instance, U.S. Pat. No. 5,683,740 and No. 5,613,583 to Voultoury et al. disclose emulsions prepared from crushed seeds of oleaginous plants comprising lipidic vesicles. In the course of the crushing process described in these patents, the oleosomes substantially lose their structural integrity. Accordingly, it is disclosed that in the crushing process 70% to 90% of the seed oil is released in the form of free oil.

On the other hand, oleosomes that are isolated from plant seeds in a structurally intact form have a recognized, practical utility. Notably, oleosomes permit the formulation of complex mixtures of aqueous compounds and oil, in the absence of exogenous emulsifiers, at room temperature, see PCT Application 2005/097059 to Guth et al., and oleosomes may be loaded with active ingredients, as described by Murray et al., PCT Application 2005/030169.

A non-destructive methodology for preparing oleosomes is disclosed by Deckers et al. in U.S. Pat. No. 6,146,645, U.S. Pat. No. 6,183,762, U.S. Pat. No. 6,210,742, No. 6,372,234, U.S. Pat. No. 6,582,710, U.S. Pat. No. 6,596,287, U.S. Pat. No. 6,599,513 and No. 6,761,914 (collectively, the "Deckers Patents"). In accordance with the Deckers Patents, a purified oleosome preparation may be obtained and used to prepare emulsions in the presence of a multiplicity of other substances, in order to achieve a desirable balance of emulsification, viscosity and appearance and render these emulsions suitable for cosmetic, food, pharmaceutical, and industrial applications, inter alia.

PCT applications 2007/122421 and 2007/122422 to Gray et al. and Galley et al., respectively, relate an oleosome-containing composition for formulation and administration to a mammal. The disclosed oleosome composition, termed the "oil curd," may be prepared from oleaginous plants and grains, and it additionally comprises extrinsic plant material, such as plant seed proteins including albumins, globulins, prolamines and glutelins, and carbohydrates. The latter, according to application 2007/122421, impart certain desirable properties, such as enhanced emulsion stability and compatibility with certain chemicals, notably detergents.

For practical applications, an oleosome preparation preferably does not undergo undesirable physical or chemical changes when various conditions may pertain, as during prolonged storage, when the oleosome preparation undergoes temperature fluctuations, as commonly occurs during transport, or when the oleosome preparation is used as an ingredient in formulation processes that may involve the use of shear forces, heating and cooling steps or the addition of reactive chemical agents. Of particular concern in this last regard are biological agents such as bacteria, fungi, mycoplasmas and the like, since their exposure to oil body preparations may well cause degradation of the oleosomes.

In order to protect oleosomes from the exposure to biological agents, preservatives may be added to oleosome preparations. Yet safety concerns and chemical reactivity/interaction with the oleosome protein coat disqualify many well-known preservatives, such as quaternary ammonium salts, formaldehyde releasing compounds, chlorinated compounds and phthalates, from use in food applications or in cosmetics, skin care, topical pharmaceutical applications, and the like. Accordingly, the most widely accepted and desirable preservatives for these applications are acid salts, such as benzoates, salicylates, sorbates, propionates, and acids such as dehydroacetic acid and ferulic acid.

In order to act as preservatives, acid or acid salt preservative agents must be substantially in their acid form, i.e., at a pH of less than 6.0 and preferably between 4.0 and 5.0. However, the present inventors have observed that, within this acidic pH range, an oleosome preparation lacks physical stability, in the sense that oleosome structure is weakened and oil "leaks" from the oleosomes; hence, it becomes problematic to mix in other ingredients, thereby to prepare a finished formulation comprised of intact oleosomes.

This problem is especially acute when oleosomes are introduced into skin care products, which frequently are formulated for compatibility with human skin, for which the pH ranges between 4.1 and 5.8. See Segger, et al., *IFSCC* 10: 2 (2007). Some topical products, such as skin exfoliants that contain acids like lactic acid, glycolic acids and salicylic acid, have an even lower pH, in a range of 3.5 and 4.5, which is far below the value at which oleosomes generally are stable physically.

In the presence of monohydric alcohols, moreover, oleosome structure is weakened, the present inventors have observed, resulting in oil leakage from the oleosome. Consequently, typical oleosome preparations are not physically stable in products, such as hand sanitizers, that require high levels of a monohydric alcohol.

To an oleosome preparation, according to the Deckers Patents, Glydant Plus®, Phenonip®, methylparaben, propylparaben, Germall 115®, Germaben II®, phytic acid and mixtures thereof may be added in order to achieve stability in the presence of bacteria, fungi, and other biological agents. The Deckers Patents do not specify the impact of these agents on the physical integrity of the constituent oleosome preparation, however.

In summary, there are shortcomings in conventional methods for manufacturing oleosome preparations. In particular, there is a need for improved methodology to stabilize oleosome preparations against undesirable physical or chemical changes that otherwise occur under a variety of conditions. Pursuant to conventional practice, it is unclear whether and how an oleosome preparation may be obtained that is preserved from a microbial standpoint and that is stable with respect to physical aspects of a preparation in an acidic pH range and in the presence of high levels of monohydric alcohol, as discussed above.

SUMMARY OF THE INVENTION

The present invention offers a system that allows for the preservation of oleosomes at a pH less than 6.0 without significant compromise to their physical stability.

Pursuant to one aspect of the invention, therefore, a method is provided for preparing a stabilized oleosome preparation. The inventive methodology comprises (a) providing an oleosome preparation and then (b) mixing the oleosome preparation in the presence of (i) a multihydric alcohol and (ii) an acidic compound capable of reducing the pH of said oleosome preparation to a pH less than 6.0.

A stabilized oleosome preparation of the invention can comprise 20% by volume of the multihydric alcohol. In a preferred embodiment, the multihydric alcohol is a non-halogenated compound. In another preferred embodiment, the multihydric alcohol is a non-aromatic diol, a non-aromatic triol, or a non-aromatic polyol.

In accordance with another aspect, the invention provides novel compositions comprising oleosomes, a multihydric alcohol, and a concentration $[H^+]$ of $10^{-6}$ moles per liter or more.

An oleosome preparation of the present invention is stable from a microbial standpoint, as well as in its physical aspects, when stored for prolonged periods at room temperature. Thus, upon storage of the stabilized oleosome preparation at room temperature for 2 years, preferably 95% or more by volume of the total oil content within the preparation will be present within the oleosomes.

The oleosome preparations obtained in accordance with the present invention are useful in the manufacture of a multiplicity of finished formulations, including, cosmetic products, food products, pharmaceutical products and industrial products, inter alia.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those of skill in the art from this detailed description.

DETAILED DESCRIPTION OF THE INVENTION

As mentioned above, the present invention relates to improved methods for the preservation of oleosome preparations. The present inventors have found that, surprisingly, a microbially stable oleosome preparation can be obtained that is additionally stable with respect to its physical aspects within the acidic pH range. This improved oleosome preparation accommodates storage under acidic conditions, exhibits improved stability when exposed to sudden temperature changes, and can be formulated into oleosome-containing finished formulations (i) that have an acidic pH, e.g., products for the topical application to the human skin, which frequently are acidic in their finished form, or (ii) that contain high levels of monohydric alcohol. Additionally, these improved oleosome preparations permit a more efficient preparation of a final formulation that incorporates the oleosome preparation as an ingredient. Notably, mixing of the water phase requires substantially less energy and time in formulation processes where an aqueous phase is mixed with the oleosome preparation that comprises an exogenously added oil phase.

Accordingly the present invention provides a method for preparing a stabilized oleosome preparation comprising:
 (a) providing an oleosome preparation; and
 (b) mixing the oleosome preparation in the presence of and
  (i) a multihydric alcohol and (ii) an acidic compound capable of reducing the pH of the oleosome preparation to a pH less than 6.0.

The oleosome preparation obtained in accordance with the invention is stable from a microbial standpoint and a physical standpoint. Preferably, the physical appearance of the oleosome preparation does not undergo any significant change when stored at room temperature for 2 years or at 45° C. for 2 months. It also is preferred that, upon storage under the foregoing conditions, 95% or more by volume of the total oil content in an oleosome preparation of the invention remains within the oleosomes; more preferably 99% or more and most preferably 100% by volume is present within the oleosomes.

Oleosome Preparation

The term "oleosome" here denotes any discrete subcellular oil or wax storage organelle obtainable from a living cell. The oleosomes may be obtained from any cell containing such organelles, including plant cells, fungal cells, yeast cells (Leber, R. et al., 1994, *Yeast* 10: 1421-28), bacterial cells (Pieper-Fürst et al., 1994, *J. Bacteriol.* 176: 4328-37), and algae cells (Roessler, P. G., 1988, *J. Phycol* (London) 24: 394-400).

In preferred embodiments of the invention the oleosomes are obtained from a plant cell, where "cell" is inclusive of cells from pollen, spores, seed and vegetative plant organs, respectively, in which oleosomes are present. Generally, see Huang, *Ann. Rev. Plant Physiol.* 43: 177-200 (1992). More preferably, the oleosomes employed in the invention is obtained from a plant seed.

Among the plant seeds useful herein, preferred are those seeds obtainable from plant species selected from the group of plant species consisting of almond (*Prunus dulcis*); anise (*Pimpinella anisum*); avocado (*Persea* spp.); beach nut (*Fagus sylvatica*); borage (*Boragio officinalis*); Brazil nut (*Bertholletia excelsa*); candle nut (*Aleuritis tiglium*); carapa (*Carapa guineensis*); cashew nut (*Ancardium occidentale*); castor (*Ricinus communis*); coconut (*Cocus nucifera*); coriander (*Coriandrum sativum*); cottonseed (*Gossypium* spp.); crambe (*Crambe abyssinica*); *Crepis alpina*; croton (*Croton tiglium*); cucumber (*Cucumis sativus*); *Cuphea* spp.; dill (*Anethum gravealis*); *Euphorbia lagascae*; evening primrose (*Oenothera biennis*); *Dimorphoteca pluvialis*; false flax (*Camolina sativa*); fennel (*Foeniculum vulgaris*); groundnut (*Arachis hypogaea*); hazelnut (*coryllus avellana*); hemp (*Cannabis sativa*); honesty plant (*Lunnaria annua*); jojoba (*Simmondsia chinensis*); kapok fruit (*Ceiba pentandra*); kukui nut (*Aleuritis moluccana*); *Lesquerella* spp., linseed/flax (*Linum usitatissimum*); lupin (*Lupinus* spp.); macademia nut (*Macademia* spp.); maize (*Zea mays*); meadow foam (*Limnanthes alba*); mustard (*Brassica* spp. and *Sinapis alba*); olive (*Olea* spp.); oil palm (*Elaeis guineeis*); oiticia (*Licania rigida*); paw paw (*Assimina triloba*); pecan (*Juglandaceae* spp.); perilla (*Perilla frutescens*); physic nut (*Gatropha curcas*); pilinut (*Canarium ovatum*); pine nut (*pine* spp.); pistachio (*Pistachia vera*); pongam (*Bongamin glabra*); poppy seed (*Papaver soniferum*); pumpkin (*Cucurbita pepo*); rapeseed (*Brassica* spp.); safflower (*Carthamus tinctorius*); sesame seed (*Sesamum indicum*); soybean (*Glycine max*); squash (*Cucurbita maxima*); sal tree (*Shorea rubusha*); Stokes aster (*Stokesia laevis*); sunflower (*Helianthus annuus*); tukuma (*Astocarya* spp.); tung nut (*Aleuritis cordata*); vernonia (*Vernonia galamensis*); and mixtures thereof. Most preferably the plant seeds are from the group of plant species comprising: rapeseed (*Brassica* spp.), soybean (*Glycine max*), sunflower (*Helianthus annuus*), oil palm (*Elaeis guineeis*), cottonseed (*Gossypium* spp.), groundnut (*Arachis hypogaea*), coconut (*Cocus nucifera*), castor (*Ricinus communis*), safflower (*Carthamus tinctorius*), mustard (*Brassica* spp. and *Sinapis alba*), coriander (*Coriandrum sativum*), squash (*Cucurbita maxima*), linseed/flax (*Linum usitatissimum*), Brazil nut (*Bertholletia excelsa*), jojoba (*Simmondsia chinensis*), maize (*Zea mays*), crambe (*Crambe abyssinica*) and eruca (*Eruca sativa*). Most preferred in this context are oil bodies prepared from safflower (*Carthamus tinctorius*).

In order to prepare oleosomes from plants, such plants are grown and allowed to set seed using agricultural cultivation practices well known to a person skilled in the art. After harvesting the seed and, if desired, removal of material such as stones or seed hulls (dehulling), by for example sieving or rinsing, and optionally drying of the seed, the seeds are subsequently processed by mechanical grinding. Preferably, a liquid phase is added prior to grinding of the seeds. This is known as "wet milling." Wet milling in oil extraction processes has been reported for seeds from a variety of plant species including mustard (Aguilar et al. 1991, *J. Texture Studies* 22: 59-84), soybean (U.S. Pat. No. 3,971,856, Cater et al., 1974, *J. Am. Oil Chem. Soc.* 51: 137-41), peanut (U.S. Pat. No. 4,025,658 and No. 4,362,759), cottonseed (Lawhon et al., 1977, *J. Am. Oil Chem. Soc.* 54: 75-80), and coconut (Kumar et al., 1995, *INFORM* 6: 1217-40).

Preferably, the liquid is water, although organic solvents such as ethanol may also be used. It also may be advantageous to imbibe the seeds for a time period from about fifteen minutes to about two days in a liquid phase prior to grinding. Imbibing may soften the cell walls and facilitate the grinding process. Imbibition for longer time periods may mimic the germination process and result in certain advantageous alterations in the composition of the seed constituents.

The seeds are preferably ground using a colloid mill. Besides colloid mills, other milling and grinding equipment capable of processing industrial scale quantities of seed may also be employed in the here described invention including: disk mills, colloid mills, pin mills, orbital mills, IKA mills and industrial scale homogenizers. The selection of the mill may depend on the seed throughput requirements as well as on the source of the seed that is employed.

Pursuant to the invention, it is important that seed oil bodies remain intact during the grinding process. Therefore, any operating conditions commonly employed in oil seed processing, which tend to disrupt oil bodies, are unsuitable for a process of the invention.

Milling temperatures are preferably between 10° C. and 90° C. More preferably, they are between 15° C. and 50° C. and most preferably between 18° C. and 30° C., while the pH is preferably maintained between 2.0 and 11.0, more preferably between 6.0 and 9.0, and most preferably between 7.0 and 9.0.

Solid contaminants, such as seed hulls, fibrous material, undissolved carbohydrates and proteins, and other insoluble contaminants are removed from the ground seed fraction. Separation of solid contaminants may be accomplished using a decantation centrifuge. Depending on seed throughput requirements, the capacity of the decantation centrifuge may be varied by using other models of decantation centrifuges, such as 3-phase decanters. Operating conditions vary depending on the particular centrifuge which is employed and must be adjusted so that insoluble contaminating materials sediment and remain sedimented upon decantation. A partial separation of the oil body phase and liquid phase may be observed under these conditions.

After the removal of insoluble contaminants, the oleosome fraction is separated from the aqueous phase. In one embodiment of the invention, a tubular bowl centrifuge is employed. In a preferred embodiment, a disc stack centrifuge is employed. Alternatively, hydrocyclones or a settling of phases under natural gravitation or any other gravity-based separation technique. It also is possible to separate the oleosome fraction from the aqueous fraction via a size-exclusion method, such as filtration, for example, membrane ultrafiltration and crossflow microfiltration.

When a centrifuge is used for this purpose, an important parameter is the size of the ring dam used to operate the centrifuge. Ring dams are removable rings with a central, circular opening of varying size, and they regulate the separation of the aqueous phase from the oleosome phase, thereby governing the purity of the oleosome fraction that is obtained. The chosen ring dam size depends on the type of centrifuge and the type of oil seed used, as well as on the desired final consistency of the oleosome preparation.

In accordance with one embodiment of the invention, safflower oleosome are obtained using an SA-7 (Westfalia) disc stack centrifuge in conjunction with a ring dam size of 69-75 mm. The efficiency of separation is further affected by the flow rate, which, in this embodiment, typically is maintained between 0.5 to 7.0 l/min. Temperatures are preferably maintained between 26° C. and 40° C.

Depending on the model centrifuge used, flow rates and ring dam sizes can be adjusted so that an optimal separation of the oleosome fraction from the aqueous phase is achieved. These adjustments will be readily apparent to a person knowledgeable in the field of process engineering.

Separation of solids and separation of the aqueous phase from the oleosome fraction may be carried out concomitantly. This can be done by means of a gravity-based separation method such as 3-phase tubular bowl centrifuge, a decanter, a hydrocyclone, or a size exclusion-based separation method.

An oleosome composition obtained at this stage in the inventive process generally is relatively crude, comprising numerous seed proteins, glycosylated and non-glycosylated, and other contaminants such as glucosinilates or its breakdown products. The invention comprehends such a composition but, in preferred embodiments, a substantial amount of seed contaminants is removed before preparing a stabilized oleosome preparation.

To accomplish removal of contaminating seed material, an oil oleosome preparation obtained upon separation from the aqueous phase, as described above, is washed at least once by resuspending the oleosome fraction in a liquid phase and centrifuging the resuspended fraction, which yields a "washed oleosome preparation."

Pursuant to the invention, washing conditions are selected generally as a function of the desired purity of the oleosome preparation. In this regard, conditions that may be varied in a controlled manner, thereby to obtain oleosome preparations of differing degrees of oleosome purity, include the makeup of the liquid phase used for washing, the washing time, the ratio of liquid phase to oleosome phase, and pH. For example, the liquid phase may be water or an organic solvent. Typically, it is advantageous to select a buffered liquid phase that (i) has a pH removed at least one pH point from the isoelectric point of the oleosomes, which point generally varies between 4 and 6, depending on the oleosome source, because such conditions facilitate separation between oleosomes and contaminants. It also is advantageous that a buffered liquid phase (ii) have a pH at which oleosomes are stable, i.e., generally in the slightly basic pH range (pH 7.0-9.0).

Suitable buffer systems for this invention are illustrated by systems comprised of sodium chloride in concentrations between 0.01 M and at 2 M, sodium bicarbonate buffers at concentrations between 25 mM and 50 mM; and low salt buffers such as 50 mM Tris-HCl at pH 7.5. In an instance when safflower oleosomes are prepared, a 45 mM sodium bicarbonate buffer at pH 8.2 is particularly suitable for obtaining relatively pure oleosome preparations.

With such a buffer one can obtain, for instance, an oleosome preparation comprising 2% or less of non-oil body proteins. Additional conditions that influence oleosome purity, in accordance with this invention, are washing time and the relative quantities of oleosome/liquid phase. By extending the washing times and/or increasing the number of washes, and by using large amounts of liquid phase, it typically is possible to obtain a higher degree of oleosome purity, albeit at the expense of yield, as one skilled in process engineering would appreciate.

Washing conditions may be adjusted as a function of the source for the prepared oleosomes. In particular, the above-described parameters of buffer composition, washing time, pH and the like may be varied to influence the constitution of the oleosome preparation, as well as the contaminating constituents, since these vary as a function of the source.

Thus, as a function of the washing conditions, an "essentially pure" oleosome preparation can be obtained; that is, the only proteins present are oil body proteins. In a preferred embodiment, the oleosome fraction contains less than 30% (w/w) of non-oil body proteins, more preferably less than 20% (w/w), and even more preferably less than 10% (w/w). In a most preferred embodiment, the oleosome fraction comprises 2% (w/w) or less of non-oilbody proteins.

Washing at a number of different pH values may be beneficial, since this will allow the step-wise removal of contaminants, particularly proteins. SDS gel electrophoresis or other analytical techniques may conveniently be used to monitor the removal of seed proteins and other contaminants upon washing of the oleosomes. Also, in instances where more than one washing step is carried out, washing conditions may vary for different washing steps.

It is not necessary to remove all of the aqueous phase between washing steps and the final washed oleosome preparation may be suspended in water, a buffer system, for example, 50 mM Tris-HCl pH 7.5, or any other liquid phase. If so desired the pH may be adjusted to any pH between pH 2.0 and 11.0, preferably between 6.0 and 9.0, and most preferably between 7.0 and 8.5. The amount of water in the oleosome preparation may be varied and, depending on the amount of water, a more or less viscous oleosome preparation can be obtained, in accordance with the invention. Thus, oleosome preparations of the invention preferably contain more than 10% and less than 65% water by volume, more preferably more than 15% and less than 50% water by volume, and most preferably more than 20% water by volume and less then 50% water by volume.

Pursuant to the invention, the process for manufacturing an oleosome preparation may be performed in batch operations or in a continuous flow process. Particularly when a disc stack centrifuge is used, a system of pumps is conveniently set up to generate a continuous flow. Illustrative of the pumps that can be employed are an air-operated, double-diaphragm pump and a hydraulic, positive-displacement or peristaltic pump.

In order to maintain a supply of homogenous consistency to the decantation centrifuge and to the tubular bowl centrifuge, homogenizers such as an IKA homogenizer may be added between the separation steps. In-line homogenizers also may be added in between various centrifuges or size exclusion-based separation devices that are employed to wash the oil body preparations. Ring dam sizes, buffer compositions, temperature and pH may differ in each washing step.

An oleosome preparation obtained in accordance with the foregoing may be stabilized via the approach described in greater detail below.

Multihydric Alcohols

In this description, the phrase "multihydric alcohol" means a hydroxyl-containing organic compound with two or more hydroxyl groups. Any multihydric alcohol may be used in the invention. Preferably, the multihydric alcohol is a water-soluble, non-halogenated multihydric alcohol of small to medium molecular weight, and less than 200,000 Daltons.

Accordingly, the employed multihydric alcohol is suitably a non-aromatic diol, triol, or polyol. When the multihydric alcohol is a diol, it may be glycol or a non-aromatic glycol derivative. Suitable glycol derivatives include butylene glycol, polyethylene glycol, propylene glycol, hexylene glycol, dipropylene glycol, hexanediol, or polybutylene glycol.

When the multihydric alcohol is a triol, it is suitably 1, 2, 6 hexanetriol or glycerol. Polymers of glycerol also may be used, including any of di-, tri-, tetra-, penta-, hexa-, septa-, octa-, nona- and decaglycerol. Also useable are lightly substituted derivatives of glycerol and polymers thereof. Lightly substituted derivatives of glycerol and polymers thereof are those molecules in which one of every six or less hydroxyl groups within those molecules have been modified. Particularly desirable substitutions are esterifications.

When the multihydric alcohol is a polyol, preferably at least one carbon atom does not have a hydroxyl group bound thereto. Glycerol and sugars such as sorbitol are exemplary of polyols that have a hydroxyl group bound to every carbon atom. Indeed, glycerol and its linear and non-linear (branched) polymeric analogues (polyglycerols), are preferred multihydric alcohols in this invention. Some ethoxylates of such polyols are suitable for use in the formulations of the present invention, provided, however, that they are liquid at room temperature or are water soluble, e.g., sorbeth 6, sorbeth 20, sorbeth 30, and sorbeth 40. Polyvinyl alcohols are illustrative of other polyols suitable in this context.

It is also possible to use multihydric sugars in accordance with the invention, including monosaccharidic sugars, such as glucose and fructose, and disaccharidic sugars such as sucrose, as well as complex multihydric sugars such as starch and cellulose. In addition, lightly substituted sugar esters may be used, provided that such esters remain multihydric.

It also is possible to use exogenous peptides and polypeptides as the multihydric alcohol in accordance with the present invention, provided that such peptides and polypeptides comprise two or more alcohol-containing amino acid residues, selected from threonine and serine. When serine- or threonine-containing peptides or polypeptides are so employed, they preferably are water-soluble and have a molecular mass between 80 Daltons and 200,000 Daltons. It is further preferred that they lack secondary or tertiary structure. Pursuant to the invention, serine- and threonine-containing peptides and polypeptides, respectively, preferably are used in purified form, although mixtures of two or more polypeptides can be employed.

In light of the foregoing description, a person skilled in chemistry will be able to identify suitable multihydric alcohols. In addition, such skilled persons will recognize that other multihydric alcohols not specifically mentioned, as well as mixtures of multihydric alcohols, may be used without departing from the spirit and scope of the present invention.

Acidic Compound

Pursuant to this invention, any acidic compound or acid salt is suitable that, when dissolved in an oleosome preparation as described above, reduces the pH of the preparation to less than about 6.0, i.e., that results in an oleosome preparation having a concentration [$H^+$] of about $10^{-6}$ moles per liter. In a preferred embodiment, the acidic compound is chosen for its capability thus to reduce the oleosome composition pH to between about 5.0 and about 6.0, more preferably to between about 5.0 and about 4.0, and most preferably to between about 4.0 and about 3.5. Illustrative of the class of suitable acidic compounds in this context are citric acid, phosphoric acid, hydrochloric acid, benzoic acid, propionic acid, glycolic acid, retinoic acid, lactic acid, sorbic acid, gluconic acid, dehydroacetic acid, hyaluronic acid, malic acid, fumaric acid, and salicylic acid, and any mixtures of these. For an oleosome preparation to formulate as a cosmetic product with exfoliation properties, the use of glycolic acid, lactic acid, retinoic acid, and/or salicylic acid is preferred.

Preparing Stabilized Oleosome Preparations

An oleosome preparation of the invention preferably comprises at least 1% oleosomes by volume. More preferably, an oleosome preparation comprises at least 5%, 10%, 20%, 30%, 40%, 50%, 60% or 75% oleosomes by volume.

To stabilize such preparations, in accordance with the invention, a multihydric alcohol preferably is added to the oleosome preparation before the acidic compound is added. Upon its addition, the multihydric alcohol is dispersed in the oleosome preparation by simple mixing or stirring, using an overhead stirrer of low shear (typically less than 500 rpm) magnetic stirrer and a stir bar, for example. In larger operations, a standard inline mixer or homogenizer may be employed, or any other means that is effective for obtaining an homogenous mixture, provided that the shear forces generated during the mixing or stirring process are modest and the oleosomes remain intact.

As mentioned above, the amount of the aqueous phase within an oleosome preparation may vary. The multihydric alcohol forms part of the aqueous phase of the oleosome preparation. When a non-proteinaceous diol, triol, or polyol is used, the multihydric alcohol concentration preferably ranges between 15% and 95% by volume of the aqueous phase of the oleosome preparation and more preferably between 25% and 75% by volume, and even more preferably between 40% and 60% by volume of the aqueous phase. Most preferably, the non-proteinaceous multihydric alcohol and water are present in equal portions within the stabilized oleosome preparation. When the multihydric alcohol is a peptide or polypeptide, then the multihydric alcohol concentration preferably ranges between 0.5% and 10% by volume of the aqueous phase of the oleosome preparation, more preferably between 0.5% and 5% by volume, and even more preferably between 0.5% and 3.5% by volume.

With the thoroughly mixed oleosome-multihydric alcohol mixture thus obtained, the pH of the preparation is adjusted by addition of an acidic compound capable of reducing the pH to 6 or less and dispersal of the acid in the oleosome preparation. The volume of acidic compound required depends on the acidic compound or mixture of acidic compounds used, but is generally preferably limited to 10% by volume. Standard instruments, such as a standard electronic pH meter, can be employed to monitor the pH of the preparation during the addition of the acidic compound, in order to ensure that the desired pH is achieved. As mentioned above, the multihydric alcohol preferably is added before the acidic compound, since it is desirable to adjust the pH as the final step. Nevertheless, it is possible to reverse the order or add both compounds together, once a reproducible process has been established and it is known what quantity of the acidic compound is required.

The foregoing process of oleosome stabilization may be performed at ambient temperature and pressure, and it is preferably performed immediately upon obtaining the oleosome preparation from its biological source. The process may be performed within 1 hour of obtaining the oleosome preparation, however, or even within 12 hours of obtaining the oleosome preparation. The stabilization process also may be included as part of the continuous process for the isolation of oleosomes, as described above.

In order to assess oleosome stability, the appearance of free oil may be monitored by visual inspection, i.e., by the appearance of oil droplets within the oleosome preparation, or by a more quantitative analytical methodology, e.g., hexane extraction (see Example 4, infra). Preferably, the physical appearance of an inventive oleosome preparation, when stored at room temperature for 2 years or at 45° C. for 2 months, does not undergo any significant changes, and none of the oleosome properties or the chemical constitution change. Upon storage of an oleosome preparation of the invention at 45° C. for 2 months, preferably 95% or more by volume of the total oil content of the oleosome preparation remains within the oleosomes (i.e., less than 5% by volume free oil), more preferably 99% or more by volume (less than 1% by volume free oil), and most preferably 100% by volume (no free oil).

The present invention further comprehends novel oleosome preparations. In another aspect, therefore, the invention provides a composition comprised of an oleosome preparation with (i) a multihydric alcohol and (ii) a concentration $[H^+]$ of $10^{-6}$ moles per liter or more. Such a composition may comprise a concentration $[H^+]$ of $10^{-5}$ moles per liter or more, or a concentration $[H^+]$ of $10^{-4}$ moles per liter or more, or a concentration $[H^+]$ of $10^{-3.5}$ moles per liter or more. The composition can contain any of the aforementioned acids and multihydric alcohols.

Utility of the Stabilized Oleosome Preparation

The stabilized oleosome preparation obtained in accordance with the present invention may be used as an ingredient to prepare a multitude of finished formulations, as outlined, for example, in the Deckers Patents, in PCT application 2005/030169, and in PCT application 2005/097059, by the addition to the oleosome preparation of one or more additional compounds. "Finished formulation" here denotes such a formulation, ready for its intended final use.

A finished formulation may be presented in a wide array of forms, including but not limited to a cream, a gel, a lotion, a waxy solid, an ointment, a salve, a paste, a spray or a milk. Advantageously, the preparation of such a formulation can be performed in the absence of exogenous emulsifiers.

Finished formulations of the present invention are illustrated by formulations for topical application to the surface area of a mammal, including personal care products, cosmetic products, topically applied pharmaceutical products, skin care products, cosmeceutical products, dermatological products, and topically applied veterinary products. Additional products that may be formulated using an oleosome preparation as described above are food, nutraceutical products, and nutritional supplements, as well as pharmaceutical and industrial products.

As mentioned previously, oleosomes prepared in accordance with the present invention are particularly useful in the manufacture of products that are held at an acidic pH in their finished form; notably, skin care products that commonly are formulated as a finished product at a pH range of the human skin, between about 5.0 and 6.0. Other personal care products that can be formulated advantageously with oleosomes prepared in accordance with the invention are exfoliating products, which typically have a pH between 3.5 and 4.5, and acne treatments, which also have a pH<5. Furthermore, oleosome preparations of the invention are useful in the manufacture of finished formulations, illustrated by personal care products such as hand sanitizers, that contain a high percentage by volume of monohydric alcohol, including ethyl alcohol.

The present invention is further described by reference to the following examples, which are illustrative only and not limiting of the invention.

Example 1

Obtaining an Oleosome Preparation from Safflower

This example describes the recovery of the oleosome fraction from safflower. The resulting preparation contains intact washed oleosomes.

Seed Decontamination.

A total of 45 kg of dry safflower (*Carthamus tinctorius*) seed was washed twice using approximate 120 L of 65° C. tap water and once using approximately 120 L of about 15° C. tap water. The washing was carried out in a barrel with screen mesh to separate the waste water.

Grinding of Seeds.

The washed seeds were poured through the hopper of a colloid mill (Colloid Mill, MZ-130 (Fryma); capacity: 350 kg/hr), which was equipped with a MZ-130 crosswise toothed rotor/stator grinding set and top loading hopper, while approximately 100 L of 45 mM sodium bicarbonate buffer of pH 8.2 was supplied through an externally connected hose prior to milling. Operation of the mill was at a gap setting of 1 R, chosen to achieve a particle size less than 100 micron at 18° C. and 30° C. All 45 kg of seeds were ground in 10 minutes.

Homogenization and Removal of Solids.

The resulting slurry was pumped into a knife in-line homogenizer (Dispax Reactor® DR 3-6/A, IKA® Works, Inc.) at a speed about 7 L/min. The output slurry was directly fed into a decantation centrifuge (NX-314B-31, Alfa-Laval) after bringing the centrifuge up to an operating speed of 3250 rpm. In 25 minutes approximately 160 kg of seed ground slurry was decanted. A Watson-Marlow (Model 704) peristaltic pump was used for slurry transfer in this step.

Oleosome Separation.

Separation of the oleosome fraction was achieved using a disc-stack centrifuge separator (SB 7, Westfalia) equipped with a three phase separating and self-cleaning bowl and removable ring dam series; maximum capacity: 83 L/min; ringdam: 69 mm. Operating speed was at ~8520 rpm. A Watson-Marlow (Model 704) peristaltic pump was used to pump the decanted liquid phase (DL) into the centrifuge after bringing it up to operating speed. This results in separation of the decanted liquid phase into a heavy phase (HP1) comprising water and soluble seed proteins and a light phase (LP1) comprising oil bodies. The oleosome fraction, which was obtained after one pass through the centrifuge, is referred to as an unwashed oleosome preparation. This unwashed oleosome fraction was then passed through a static inline mixer, mixing with 45 mM sodium bicarbonate (pH 8.2) buffer (35° C., 4 L/min) into a second disc-stack centrifuge separator (SA 7, Westfalia); maximum capacity: 83 L/min; ringdam: 73 mm. Operating speed was at 8520 rpm. The separated light phase (LP2) comprising oleosome was then passed through another static inline mixer mixing with pH8, 45 mM sodium bicarbonate (pH 8.2) buffer (35° C., 4 L/min) into the third disc-stack centrifuge separator (SA 7, Westfalia); maximum capacity: 83 L/min; ringdam: 75 mm. Operating speed was at ~8520 rpm. The entire procedure was carried out at room temperature. The preparations obtained following the second separation are all referred to as the washed oleosome preparation.

Example 2

Preparing a Safflower Oleosome Preparation Stabilized at a pH of about 4.5 in the Presence of a Multihydric Alcohol, Glycerin To 100 g of a 75% solids dispersion of safflower oleosomes was added 25 g of pure glycerin (99%+ purity) with low shear mixing. This reduced the total oleosome level to 60% (water 20%, glycerin 20%). The pH of this dispersion is typically >8.5. Added to the dispersion with low shear stirring was 1.25 g of a commercial preservative Geogard Ultra which consists of a blend of glucono delta lactone and benzoic acid which reduced the pH of the dispersion to 4.2-4.5. The dispersion passed microbial challenge testing and no leakage of the oleosomes was observed after 6 months at 25° C.

Example 3

Preparing a Safflower Oleosome Preparation Stabilized at a pH of about 4.5 in the Presence of a Multihydric Alcohol, Decaglycerin To 100 g of a 75% solids dispersion of safflower oleosomes were added 25 g of Natrulon H-10 (decaglycerin, from Lonza) under propeller at 400 rpm for 10 minutes. This reduced the total oleosome level to 60% (water 20%, decaglycerin 20%). The pH of this dispersion was typically approximately 7.5. Added to the dispersion, with low shear stirring, was 1.25 g of Geogard® Ultra, a commercial preservative from Lonza, which consists of a blend of glucono delta lactone and benzoic acid. Once equilibrated, the preservative reduced the pH of the dispersion to 4.5.

Example 4

Stability of a Safflower Oleosome Preparation at pH of about 4.5 in the Presence and Absence of a Multihydric Alcohol Stabilized oleosome preparations were prepared in accordance with Examples 1 and 2.

| Oleosome Type | pH <4.5 |
|---|---|
| Stabilized Oleosome Formulation | Formulation is stable No leakage (visual inspection) |
| Non stabilized Oleosome Formulation | Separation of aqueous and oil layer (visual inspection) |

The following methodology may be used in order to assess, in a quantitative manner, the stability of an oleosome preparation:
1. Label and weigh 4 (four) clean and dry 16×100 mm screw-cap Pyrex test tubes (+/−0.0001 g) per sample. Label with sample name A and T1, sample name B and T1, then repeat replacing T1 with T2. Record values. Add 1 ml of oleosome sample.
2. Invert sample container 10 to 12 times to mix sample thoroughly and immediately pipet 1 ml of sample using a wide bore 1 ml pipet tip.
3. Transfer sample in duplicate to tube numbers T1.
4. Clean off any sample on the top of the tube and reweigh the tubes containing the samples (+/−0.0001 g). Record values.
5. Add 3 ml of pure hexane to the tubes with the sample, cap tube with teflon-lined cap, shake and mix vigorously for 30 seconds, endeavoring to incorporate any sample stuck to the sides of the tube.
6. Centrifuge sample in clinical centrifuge at full speed at 3,000 rpm for 2 minutes to pellet sample. Free oil will remain in the hexane (top layer) and oilbodies/rest of sample will pellet.
7. Using a glass transfer pipette, carefully remove as much of the hexane containing the free oil from the top of the sample as possible and transfer to tube T2. Place tube T2 in heating block and repeat steps 6 and 7. Subsequent extractions will be placed in T2.
8. Evaporate the hexane from the samples by subjecting the tubes to a gentle stream of high purity $N_2$ gas (Pierce Reacti-Vap manifold) while heating the block to 40-45° C. Evaporate the hexane for at least one hour.
9. Reweigh the tubes containing free oil and return to $N_2$ evaporation for 15 minutes.
10. Reweigh the tubes again until two successive readings are the same (+/−0.0002).

This represents the free oil with all solvents removed.
Sample Calculations:

| Sample mass: | |
|---|---|
| Mass tube 1: | 11.9365 g |
| Mass tube 1 + sample: | 12.4022 g |
| Sample mass: | 0.4657 g |
| Mass tube 2: | 12.0706 g |
| Mass tube 2 + sample: | 12.0865 g |
| Sample mass: | 0.0159 g |

Breakdown of oil bodies caused by pure hexane = 0.0040 g per extraction
Free oil as a % of the sample: (sample mass T2 − correction)/(sample in T1) × 100 = (0.0159 − 0.0120/0.4657) × 100 = 0.84%

Example 5

Preparation of a Skin Cream Comprising a Safflower Oleosome Preparation Stabilized at a pH of about 6 or Less in the Presence of a Multihydric Alcohol

| INGREDIENT | PERCENTAGE |
|---|---|
| Phase 1 Oil Phase | |
| Glycerin stabilized oleosomes (consisting of 59.33% oleosomes, 19.33% water, 19.33% glycerin, 1% Geogard Ultra) | 10.0% |
| Decaglyceryl decaoleate | 5.0% |
| Phase 2 Water Phase | |
| Water | 70.2% |
| Decaglycerin | 5.0% |
| NaOH (0.25N) | 6.20% |
| Phase 3 | |
| Aristoflex AVC (Ammonium Acryloyldimethyl Taurate/VP Copolymer) | 1.3% |
| Phase 4 | |
| Geogard Ultra (Glucono delta lactone and benzoic acid) | 2.0% |
| Phase 5 | |
| Fragrance | 0.30% |

Procedure
1. Add Phase 1 ingredients together with low shear stirring.
2. Add the Phase 2 ingredients together, the pH is approximately 11.
3. Slowly add Phase 2 to Phase 1 with low shear mixing. Homogeneity will be realized very quickly (usually less than a minute).
4. Add Phase 3 slowly with high sheer mixing (500 rpm).

5. Add Phase 4 and Phase 5 and stir for another 5 minutes. Check pH and adjust to between 5 and 6.

Example 6

Preparation of an Exfoliating Product Comprising a Safflower Oleosome Preparation Stabilized at a pH of about 4.0 in the Presence of a Multihydric Alcohol

| INGREDIENT | PERCENTAGE |
|---|---|
| Phase 1 Oil Phase | |
| Glycerin stabilized oleosomes (consisting of 59.33% oleosomes, 19.33% water, 19.33% glycerin, 1% Geogard Ultra) | 12.5% |
| Phase 2 Water Phase | |
| Glycolic acid (70% active) | 8.0% |
| Water | 74.25% |
| Sodium Hydroxide QS to pH 4.0 | 1.5% |
| Phase 3 | |
| Aristoflex AVC (Ammonium Acryloyldimethyl Taurate/VP Copolymer) | 1.5% |
| Phase 4 | |
| Geogard Ultra (Glucono delta lactone and benzoic acid) | 2.0% |
| Phase 5 | |
| Fragrance | 0.25% |

Procedure
1. Add the Phase 2 ingredients together with cooling and stirring, check the pH. It should be approximately 4.0.
2. Slowly add Phase 2 to Phase 1 with low shear mixing. Homogeneity will be realized very quickly (usually less than a minute).
3. Add Phase 3 slowly with high sheer mixing (500 rpm). It will at first coagulate and then gradually redisperse and thicken the mixture.
4. Add Phase 4 and Phase 5 and stir for another 5 minutes.

Example 7

Preparation of a Moisturizing Lotion Comprising a Safflower Oleosome Preparation Stabilized at a pH of about 5.2 in the Presence of a Multihydric Alcohol

| INGREDIENT | PERCENTAGE |
|---|---|
| Phase 1 | |
| Glycerin stabilized oleosomes (consisting of 59.33% oleosomes, 19.33% water, 19.33% glycerin, 1% Geogard Ultra) | 10% |
| Decaglyceryl Decaoleate | 5% |
| Octyl Methoxycinnamate | 2% |
| Phase 2 | |
| Glycerin | 5% |
| Water | 74.9% |
| Phase 3 | |
| Aristoflex AVC (Ammonium Acryloyldimethyl Taurate/VP Copolymer) | 1.1% |
| Phase 4 | |
| Geogard Ultra (Glucono delta lactone and benzoic acid) | 2.0% |
| NaOH | QS |

Procedure
1. Mix Phase 1 for 8-10 min at 300-500 rpm.
2. Add Phase 2 to Phase 1 incrementally while mixing at 500 rpm over 10 min.
3. Add Phase 3 and mix at 700 rpm for an additional 5 minutes.
4. Add Phase 4 and adjust pH to 5.0-5.5 with NaOH with stirring (700 rpm).
5. Viscosity, 70,000 cp (spindle TC @ 2 rpm and 25° C.).

Example 8

Preparation of an Exfoliating Cream Comprising a Safflower Oleosome Preparation Stabilized at a pH of about 4.0 in the Presence of a Multihydric Alcohol

| INGREDIENT | PERCENTAGE |
|---|---|
| Phase 1 | |
| Glycerin stabilized oleosomes (consisting of 59.33% oleosomes, 19.33% water, 19.33% glycerin, 1% Geogard Ultra) | 10% |
| Decaglyceryl Decaoleate | 5% |
| Octyl Methoxycinnamate | 2% |
| Phase 2 | |
| Glycolic Acid (70%) | 8% |
| Water | 73.5% |
| Phase 3 | |
| Aristoflex AVC (Ammonium Acryloyldimethyl Taurate/VP Copolymer) | 1.1% |
| Phase 4 | |
| Dehydroacetic acid (DHA), salicylic acid, benzoic acid, and benzethonium chloride (Geogard 361) | 0.4% |
| NaOH | QS |

Procedure
1. Mix Phase 1 for 8-10 min at 300-500 rpm.
2. Add Phase 2 to Phase 1 incrementally while mixing at 300-500 rpm over 10 minutes.
3. Add Phase 3 and mix at 700 rpm for an additional 5 minutes.
4. Add Phase 4 and adjust pH to 4.0 with NaOH with stirring (700 rpm) for 2 minutes.

5. Viscosity, approx. 150,000 cp (spindle TC @ 2 rpm and 25° C.).

Example 9

Preparation of a Natural Moisturizer Comprising a Safflower Oleosome Preparation Stabilized at a pH of about 5.3 in the Presence of a Multihydric Alcohol

| INGREDIENT | PERCENTAGE |
|---|---|
| Phase 1 | |
| Glycerin stabilized oleosomes (consisting of 59.33% oleosomes, 19.33% water, 19.33% glycerin, 1% Geogard Ultra) | 10% |
| Decaglyceryl Decaoleate | 5% |
| TiO2 (hydrophobically modified) | 2% |
| Phase 2 | |
| Glycerin | 5% |
| Water | 74.9% |
| Phase 3 | |
| Carrageenan (Genuvisco) | 1.1% |
| Phase 4 | |
| Geogard Ultra (Glucono delta lactone and benzoic acid) | 2.0% |
| NaOH | QS |

Procedure
1. Mix Phase 1 for 10 min at 300-500 rpm.
2. Add Phase 2 to Phase A incrementally while mixing at 300-500 rpm over 10 minutes.
3. Add Phase 3 and mix at 700 rpm for an additional 5 minutes.
4. Add Phase 4 and stir for 2 minutes at 700 rpm.
5. Adjust pH to 5.0-5.5 with NaOH.
6. Viscosity, approximately 40,000 cps.

Example 10

Preparation of Natural Moisturizer Comprising a Safflower Oleosome Preparation Stabilized at a pH of about 5.7 in the Presence of a Multihydric Alcohol

| INGREDIENT | PERCENTAGE |
|---|---|
| Phase 1 | |
| Glycerin stabilized oleosomes (consisting of 59.33% oleosomes, 19.33% water, 19.33% glycerin, 1% Geogard Ultra) | 10% |
| TiO2 (hydrophobically modified) | 1% |
| Phase 2 | 10% |
| Glycerin | |
| Water | 76.75% |
| Phase 3 | |
| Carrageenan (Genuvisco) | 1.1% |
| Phase 4 | 1.15% |
| Glucose oxidase/lacto peroxidase type preservative | |
| HCl | QS |

Procedure
1. Mix Phase 1 for 10 min at 300-500 rpm.
2. Add Phase 2 to Phase 1 incrementally while mixing at 300-500 rpm over 10 min.
3. Add Phase 3 and mix at 700 rpm for an additional 5 minutes.
4. Add Phase 4 and stir for 2 minutes at 500 rpm.
5. Adjust pH to 5.5-6.0 with HCl.
6. Viscosity, approximately 42,000 cps.

Example 11

Preparation of Moisturizing Comprising a Safflower Oleosome Preparation Stabilized at a pH of about 5.3 in the Presence of a Multihydric Alcohol (Decaglycerin)

| INGREDIENT | PERCENTAGE |
|---|---|
| Phase 1 | |
| Standard oleosomes (75% oleosomes, 25% water) | 10.0 |
| Natrulon H-10 (Decaglycerin/Water) | 2.50 |
| Phase 2 | |
| Polyaldo DGDO (10-10-0) (Polyglyceryl-10 Decaoleate) | 5.00 |
| Uvinul MC 80 (Ethylhexyl Methoxycinnamate) | 2.00 |
| Fragrance | 0.50 |
| Phase 3 | |
| DI Water | 77.90 |
| Phase 4 | |
| Geogard Ultra (Gluconolactone/Sodium Benzoate) | 1.00 |
| Aristoflex AVC (Ammonium Acryloyldimethyltaurate/VP Copolymer) | 1.10 |

Procedure
1. Prepare the decaglycerin stabilized oleosome preparation by combining Phase 1 under propeller and mixing for 10 minutes at 400 rpm.
2. Add Phase 2 in the order of appearance and mix for an additional 10 minutes.
3. Add Phase 3 in increments and mix under propeller for 20 minutes, slowly increasing speed from 400 to 650 rpm.
4. Add Phase 4 in order of appearance and mix at 650 rpm until the batch is uniform and thickened. Adjust pH to 5.2-5.5.

Example 12

Preparation of a Hand Sanitizer Comprising a Safflower Oleosome Preparation Stabilized in the Presence of a Multihydric Alcohol

| INGREDIENT | PERCENTAGE |
|---|---|
| Phase 1 | |
| Glycerin stabilized oleosomes (consisting of 59.33% oleosomes, 19.33% water, 19.33% glycerin, 1% Geogard Ultra) | 12.5 |
| Fragrance | 0.3 |

-continued

| INGREDIENT | PERCENTAGE |
|---|---|
| Phase 2 | |
| Dionized water | 30.0 |
| Phase 3 | |
| Ethyl alcohol | 55.0 |
| Phase 4 | |
| Methocel J75M (Hydroxypropyl Methylcellulose) Amercol | 1.0 |
| Phase 5 | |
| Sodium hydroxide solution | QS |
| Citric acid solution | QS |

Procedure
1. Under propeller, combine Phase 1 ingredients and mix for 10 minutes at 400 rpm.
2. Slowly add Phase 2 in increments. Increase speed to 600 rpm and mix for 10 minutes.
3. After all water is in, slowly start adding Phase 3 and mix for 10 minutes.
4. Add Phase 4 slowly and mix for 20 minutes to properly disperse the gum.
5. Add sodium hydroxide to increase the pH to 8.5-9.0 to thicken the gum. Mix until uniform.
6. Add citric acid to adjust the pH to 6.5-7.0.

Example 13

Preparation of a Margarine Comprising a Safflower Oleosome Preparation Stabilized in the Presence of a Multihydric Alcohol

| INGREDIENT | GRAMS |
|---|---|
| Palm Oil | 1500 |
| Soy Oil | 1653 |
| Water | 751.2 |
| Salt | 72 |
| Glycerin stabilized oleosomes (consisting of 59.33% oleosomes, 19.33% water, 19.33% glycerin, 1% Geogard Ultra) | 10.8 |
| Lecithin | 8 |
| Lactic Acid | 1.8 |
| Beta Carotene | 0.28 |
| Potassium Sorbate | 3 |

Procedure
1. Add the soy oil to a kettle. With agitation heat to 130° F.
2. Add the palm oil and maintain temperature.
3. With agitation add the lecithin. Mix for 5 minutes.
4. In a separate kettle add the water and heat to 140° F.
5. With agitation add the salt, lactic acid, and potassium sorbate. Mix for 5 minutes.
6. Add the glycerin-stabilized oleosomes. Mix for 5 minutes.
7. With agitation add the beta carotene to the oil blend.
8. Combine the oil and water blends and maintain temperature at 130° F. Mix for 10 minutes.
9. Undertake homogenization and ultra-high temperature processing.

While the present invention has been described with reference to what are presently considered to be preferred examples, it is to be understood that the invention is not limited to the disclosed examples. To the contrary, the invention is intended to cover various modifications and equivalent arrangements included within the spirit and scope of the appended claims.

All publications, patents, and patent applications are incorporated by reference in their entirety to the same extent as if each such publication, patent, or patent application was specifically and individually indicated to be incorporated by reference in its entirety.

What we claim is:
1. A method for making a stabilized safflower oleosome preparation or a stabilized almond oleosome preparation consisting essentially of mixing a safflower oleosome or an almond oleosome with glycerin and glycolic acid to produce said stabilized safflower oleosome preparation or said stabilized almond oleosome preparation.
2. The method of claim 1, wherein said stabilized safflower oleosome preparation is produced.
3. The method of claim 1, wherein said stabilized almond oleosome preparation is produced.

* * * * *